United States Patent
Gabel et al.

(10) Patent No.: US 11,447,637 B2
(45) Date of Patent: Sep. 20, 2022

(54) ASPHALT EMULSION COMPOSITION AND METHOD OF TREATING A PAVEMENT SURFACE

(71) Applicant: Ecolab USA Inc., St. Paul, MN (US)

(72) Inventors: Robert Gabel, Georgetown, TX (US); Glenda Vale, Corsicana, TX (US); Eric Bauch, Corsicana, TX (US); Chenthamarkshan Nair, Corsicana, TX (US); Adam Meyers, Waxahachie, TX (US)

(73) Assignee: Ecolab USA Inc., St. Paul, MN (US)

( * ) Notice: Subject to any disclaimer, the term of this patent is extended or adjusted under 35 U.S.C. 154(b) by 82 days.

(21) Appl. No.: 16/806,416

(22) Filed: Mar. 2, 2020

(65) Prior Publication Data

US 2020/0291233 A1    Sep. 17, 2020

Related U.S. Application Data (60) Provisional application No. 62/819,124, filed on Mar. 15, 2019.

(51) Int. Cl.

| | |
|---|---|
| *C08K 5/09* | (2006.01) |
| *C08K 5/092* | (2006.01) |
| *C08L 95/00* | (2006.01) |
| *C08K 3/22* | (2006.01) |
| *C08K 3/24* | (2006.01) |
| *C08K 5/05* | (2006.01) |
| *C08K 5/103* | (2006.01) |
| *C08K 5/13* | (2006.01) |
| *C08K 5/17* | (2006.01) |
| *C08K 5/19* | (2006.01) |
| *C08K 5/3445* | (2006.01) |
| *E01C 7/35* | (2006.01) |
| *E01C 11/00* | (2006.01) |

(52) U.S. Cl.
CPC ............ *C08L 95/005* (2013.01); *C08K 3/22* (2013.01); *C08K 3/24* (2013.01); *C08K 5/05* (2013.01); *C08K 5/09* (2013.01); *C08K 5/103* (2013.01); *C08K 5/13* (2013.01); *C08K 5/175* (2013.01); *C08K 5/19* (2013.01); *C08K 5/3445* (2013.01); *E01C 7/353* (2013.01); *E01C 11/005* (2013.01); *C08K 2003/2206* (2013.01); *C08K 2003/2217* (2013.01)

(58) Field of Classification Search
CPC .... C08L 95/005; C08L 2555/28; E01C 7/353; E01C 11/005; C08K 3/22; C08K 3/24; C08K 5/05; C08K 5/09; C08K 5/103; C08K 5/13; C08K 5/175; C08K 5/19; C08K 5/3445

See application file for complete search history.

(56) References Cited

U.S. PATENT DOCUMENTS

| | | | |
|---|---|---|---|
| 4,250,048 A | 2/1981 | Leveskis | |
| 4,276,185 A | 6/1981 | Martin | |
| 4,436,767 A | 3/1984 | Grossi et al. | |
| 5,096,495 A | 3/1992 | Schilling et al. | |
| 5,352,285 A | 10/1994 | Krivohlavek | |
| 5,928,418 A | 7/1999 | Tamaki et al. | |
| 6,048,905 A * | 4/2000 | Asamori | B01F 17/0042 106/277 |
| 6,667,382 B1 | 12/2003 | Isobe et al. | |
| 7,172,703 B2 | 2/2007 | Javora et al. | |
| 7,312,262 B2 | 12/2007 | Donelson et al. | |
| 7,902,277 B2 | 3/2011 | Reinke et al. | |
| 8,287,945 B2 | 10/2012 | Takamura et al. | |
| 2002/0183401 A1 | 12/2002 | Wates et al. | |
| 2006/0229389 A1 | 10/2006 | Howe et al. | |
| 2007/0006777 A1 * | 1/2007 | Setliff | C04B 28/021 106/697 |
| 2009/0176684 A1 * | 7/2009 | Gardner | C11D 3/34 510/392 |
| 2010/0288644 A1 * | 11/2010 | Brown | C10M 173/00 205/80 |
| 2014/0329938 A1 | 11/2014 | Coe | |
| 2014/0356526 A1 | 12/2014 | O'Connell et al. | |
| 2015/0376410 A1 | 12/2015 | Issariyakul | |
| 2018/0171147 A1 | 6/2018 | Allen et al. | |

FOREIGN PATENT DOCUMENTS

| | | | |
|---|---|---|---|
| EP | 2 907 853 A1 | 8/2015 | |
| FR | 3 020 065 A1 | 10/2015 | |
| GB | 1 438 665 | 6/1976 | |
| JP | 08302393 A | * 11/1996 | |
| WO | 00/68329 A1 | 11/2000 | |
| WO | 2005/100481 A1 | 10/2005 | |
| WO | 2014/006340 A2 | 1/2014 | |
| WO | 2014/063216 A1 | 5/2014 | |

OTHER PUBLICATIONS

Machinne translation into English of JP-08302393-A; Aihara et al (Year: 1996).*
Chi et al; Prevention and Control of Corrosion-Induced Asphaltene Deposition; (Year: 2016).*
International Search Report and Written Opinion relating to PCT/US2020/020692 dated May 27, 2020, 8 pages.
Jain, P. K., et al., "Studies on Mitigation of Moisture Damage in Bituminous Pavements," Indian Journal of Engineering & Materials Sciences, Feb. 2007, pp. 48-54, vol. 14.

* cited by examiner

*Primary Examiner* — Karuna P Reddy
(74) *Attorney, Agent, or Firm* — Stinson LLP (57) ABSTRACT

Compositions and methods are provided for treating a pavement such as by microsurfacing or slurry sealing. The compositions contain iron chelants that are effective in reducing discoloration of the pavement surface.

27 Claims, 2 Drawing Sheets

(2 of 2 Drawing Sheet(s) Filed in Color)

ASPHALT EMULSION COMPOSITION AND METHOD OF TREATING A PAVEMENT SURFACE

CROSS REFERENCE TO RELATED APPLICATIONS

This application claims the benefit of provisional patent application Ser. No. 62/819,124, filed Mar. 15, 2019.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Compositions and methods for treating pavement surfaces are provided. More specifically, the compositions and methods minimize discoloration of asphalt pavement treatments.

BACKGROUND OF THE INVENTION

Pavement surfaces such as roadways, driveways and parking lots often show signs of aging and deterioration within 1 to 7 years and require repair or resurfacing to seal the surface from water intrusion, improve pavement appearance, repair wheel rutting, and protect from oxidation and UV damage and oil and gasoline spills. Existing pavement surfaces are repaired or resurfaced every two to three years or so by various techniques such as slurry sealing and microsurfacing to form a cured layer of a dry asphalt coating on the pavement surface. The emulsified asphalt surface treatment can be used to maintain and preserve the pavement surface to avoid the high cost of replacing the pavement. The process involves the use of aggregate rock, water and an asphalt emulsion. Microsurfacing is a quick setting emulsion designed to allow traffic to run on the surface in one hour or less. Slurry sealing can be slow setting or quick setting depending on the choice of emulsifiers and other additives used, the type of aggregate used, and the temperature.

These compositions are prepared by loading an asphalt emulsion, aggregate and water into a vehicle that prevents contact of these materials. The asphalt emulsion, aggregate and water are mixed in situ in a spreader box while the vehicle moves over the surface of the pavement and the mixture is spread onto the road. Alternatively, the aggregate can be applied as a layer to a surface of pavement before the asphalt emulsion is applied.

The surfacing composition should flow easily onto the pavement surface and not solidify prematurely. Water is used in the asphalt emulsion to obtain flowable consistency while being resistant to separation from the aggregate. When the mixture is applied, demulsification of the asphalt emulsion takes place as soon as possible so that the mixture can rapidly set up and harden.

It is desirable to form a black treated pavement to provide the appearance of a new pavement surface. However, discoloration has been observed and there is a need to prevent discoloration or browning of the treated pavement surface.

BRIEF SUMMARY OF THE INVENTION

A composition for preparing an asphalt emulsion is provided. The composition can comprise an emulsifier and an iron chelant.

An asphalt emulsion composition for surfacing pavement is also provided. The asphalt emulsion composition can comprise the composition for preparing the asphalt emulsion as described above, and an asphalt.

A method of treating a surface of a pavement is also provided. The method can comprise: applying the asphalt emulsion composition as described herein to the surface of the pavement or to a layer comprising a mineral aggregate on the surface of the pavement to form a treated surface; and curing the treated surface.

Another method of treating a surface of a pavement is also provided. The method can comprise: combining the composition for preparing an asphalt emulsion as described herein, an asphalt and water to form an asphalt emulsion composition; applying the asphalt emulsion composition to the surface of the pavement or to a layer comprising a mineral aggregate on the surface of the pavement to form a treated surface; and curing the treated surface.

Yet another method of treating a surface of a pavement is also provided. The method can comprise: combining an iron chelant and an asphalt emulsion comprising asphalt, an emulsifier and water to form a surfacing composition; applying the surfacing composition to the surface of the pavement or to a layer comprising a mineral aggregate on the surface of the pavement to form a treated surface; and curing the treated surface.

These methods can further comprise mixing mineral aggregate with the asphalt emulsion composition or surfacing composition before application.

These methods can further comprise applying a layer of mineral aggregate on the treated surface before the treated surface is completely cured.

A treated pavement is also provided. The treated pavement can comprise a pavement and a surface layer on an exposed surface of the pavement, the surface layer containing an iron chelant, an emulsifier, and an asphalt. The surface layer can optionally further contain mineral aggregate. The treated pavement can optionally further comprise a layer of mineral aggregate on at least a portion of the surface layer.

Other objects and features will be in part apparent and in part pointed out hereinafter.

BRIEF DESCRIPTION OF THE SEVERAL VIEWS OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

The compositions of the invention are used in methods of treating a pavement, such as microsurfacing, chip sealing, double surface treating, triple surface treating, cape sealing, sandwich sealing, sand sealing, slurry sealing, seal coating or fog sealing. The compositions are effective in preventing or minimizing discoloration of the treated pavement.

More specifically, a brown discoloration can result when asphalt emulsions are used in resurfacing an exposed surface of an existing pavement such as a road, parking lot or driveway. Without being bound to any particular theory, it is believed that free iron present in asphalt and/or mineral aggregate used in the resurfacing process causes formation of the brown discoloration of the treated surface when the iron is present in an amount of 2% or more of the asphalt and/or mineral aggregate. Such discoloration can be prevented or minimized by incorporating an iron chelant in the asphalt emulsion composition that is used in resurfacing the pavement. The iron chelant is believed to form a complex with the free iron to remove the free iron that is present in asphalt and/or mineral aggregate used in the resurfacing process.

One aspect of the invention is directed to a composition for preparing an asphalt emulsion. The composition can comprise an emulsifier and an iron chelant.

The iron chelant can comprise, but is not limited to:

a carboxylic acid derivative of an alkylamine having the formula 1:

(1)

wherein:

$R_1$, $R_2$, $R_4$, $R_5$, and $R_6$ are each individually hydrogen, $C_6$-$C_{30}$ alkyl, or —$R_7$COOH;

$R_3$ and $R_7$ are each individually alkylene;

n is 0, 1, or 2; and at least one of $R_1$, $R_2$, $R_4$, $R_5$, and $R_6$ is $C_6$-$C_{30}$ alkyl, and at least one of $R_1$, $R_2$, $R_4$, $R_5$, and $R_6$ is —$R_7$COOH; catechol; alkyl catechol such as 4-tert butyl catechol; 1,2-dihydroxybenzene-3,5-disulfonic acid; an hydroxypyridine N-oxide; a thiosulfate salt; an alkanolamine; a polyalkyleneimine; an amino-substituted acrylic monomer or polymer; a morpholine; urea; a guanidine salt; a pyrrole; polyvinylpyrrole; a pyrazole; a pyridine; an ortho alkoxy-substituted pyridine; an amino phenol; an ortho amino phenol; an amino cresol; ortho anisidine; an amine acetate surfactant; a mercapto surfactant; or a derivative or combination thereof. Preferably, iron chelant comprises catechol; alkyl catechol; the carboxylic acid derivative of the alkylamine; or a derivative or combination thereof.

When the iron chelant comprises the carboxylic acid derivative of the alkylamine, preferred substituents include where $R_1$ is $C_8$-$C_{22}$ alkyl; $R_2$, $R_4$, $R_5$, and $R_6$ are each individually hydrogen or —$R_7$COOH; $R_3$ and $R_7$ are each individually $C_1$-$C_6$ alkylene; n is 0, 1 or 2; and at least one of $R_1$, $R_2$, $R_4$, $R_5$, and $R_6$ is —$R_7$COOH. For example, one, two or three of $R_1$, $R_2$, $R_4$, $R_5$, and $R_6$ can be —$R_7$COOH; each $R_3$ can be individually $C_2$-$C_4$ alkylene; each $R_7$ can be individually $C_1$-$C_6$ alkylene; and n can be 0 or 1. Alternatively, one, two or three of $R_1$, $R_2$, $R_4$, $R_5$, and $R_6$ can be —$R_7$COOH; each $R_3$ can be individually $C_2$-$C_4$ alkylene; each $R_7$ can be individually $C_1$-$C_4$ alkylene; and n can be 0. Preferably, $R_1$ is tallow, $R_3$ is propylene, and $R_7$ is methylene.

Preferably, the carboxylic acid derivative of the alkylamine comprises mono-, di- and tri-acetic acid derivatives of tallow diamine (with tallow, for example, derived from a mixture of $C_{14}$-$C_{22}$ beef tallow fats as described in U.S. Pat. No. 7,172,703). Such mono-, di- and tri-acetic acid derivatives of tallow diamine include compounds or mixtures of any of the compounds of the following formulae 2A-2E:

(2A)

(2B)

(2C)

(2D)

(2E)

wherein R is tallow. This iron chelant is commercially available as TD3A-83 (Ecolab, St. Paul, Minn.).

The emulsifier can be any emulsifier used in the emulsified asphalt industry. The emulsifier can comprise, but is not limited to, a tallow amine, a tallow diamine, a diquaternary amine, a tallow tetramine, a tallow diquaternary amine, oleic acid, a tall oil, a tall oil resin, a tall oil imidazoline, a tall oil fatty acid, a soybean fatty acid, a tall oil fatty acid and soybean fatty acid polyalkyleneamine condensate, a lignosulphonate, a lignin, a lignin amine, an imidazoline, an amidoamine, an amidopolyamine, a triglyceride, an ethoxylate, an alkoxylate, a carboxylate, a polycarboxylate, a sulfonate, a fatty amine, a fatty acid, a rosin acid, alkylphenol alkoxylate such as nonylphenol ethoxylate, or a combination thereof.

The composition can be used to prepare an asphalt emulsion for treating a pavement surface. The emulsifier can aid in dispersion, suspension and stabilization of the asphalt emulsion.

One of ordinary skill can select an appropriate emulsifier to provide anionic, cationic or nonionic character to the asphalt emulsion that is formed.

The skilled person can also select an emulsifier to function as a rapid set, quick set or slow set asphalt emulsion as is well known in the art.

The composition for preparing an asphalt emulsion can further comprise an organic solvent. Any organic solvent typically used in the asphalt paving industry is suitable.

The organic solvent can comprise, but is not limited to, alcohols (methanol, ethanol, propanol, isopropanol, butanol, 2-ethylhexanol, hexanol, octanol, decanol, 2-butoxyethanol), alkylene glycols (methylene glycol, ethylene glycol, 1,2-propylene glycol, 1,3-propylene glycol), alkylene glycol alkyl ethers (diethyleneglycol monomethyl ether, diethylene glycol monoethyl ether, ethylene glycol monobutyl ether, ethylene glycol dibutyl ether), alkanes and cycloalkanes (pentane, hexane, cyclohexane, methylcyclohexane, heptane, decane, dodecane), diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The composition can further comprise water, a base and/or an acid.

The base can comprise sodium hydroxide, magnesium hydroxide, potassium hydroxide, calcium hydroxide, ammonium hydroxide, sodium carbonate, sodium bicarbonate, or a combination thereof.

The acid can comprise an inorganic acid or an organic acid.

The composition can comprise from about 5 to about 30 wt. % of the iron chelant and about 40 to about 95 wt. % of the emulsifier based on the total weight of the composition.

The composition can further comprise from about 0.1 to about 25 wt. %, from about 5 to about 20 wt. %, or from about 10 to about 20 wt. % of the organic solvent based on the total weight of the composition.

The composition can further comprise from about 0.1 to about 10 wt. %, from about 0.1 to about 6 wt. %, or from about 0.1 to about 4 wt. % water based on the total weight of the composition.

The asphalt emulsion composition can be rapid setting, quick setting, or slow setting as is known in the art. Rapid setting asphalt emulsions generally set in less than one hour. Quick setting asphalt emulsions set in an hour or two. Slow setting asphalt emulsions can take from several hours to one or more days to set. For example, the asphalt emulsion composition can be a cationic quick set asphalt emulsion.

Representative compositions for preparing an asphalt emulsion are provided in Table 1 below.

TABLE 1

| Component | Compositions for Preparing an Asphalt Emulsion | | | | | | | | |
|---|---|---|---|---|---|---|---|---|---|
| | A | B | C | D | E | F | G | H | I |
| Iron Chelant | | | | | | | | | |
| Mixture of Acetic acid derivatives of tallowdiamine | 40.0 | | 22.0 | | | 20.0 | | 10.0 | |
| Catechol | | | | 17.9 | | | | | |
| tert-Butylcatechol | | 27.5 | | | 17.7 | | | | |
| Guanidine salt | | | | | | | 12.2 | | |
| Pyridine | | | | | | | | | 5.0 |
| Emulsifier | | | | | | | | | |
| Tall oil fatty acid and soybean fatty acid polyalkylene-amine condensate | 60.0 | | | 65.1 | 65.8 | 80.0 | 85.7 | 90.0 | |
| Nonylphenol ethoxylate | | | 60.4 | | | | | | |
| Imidazoline | | | | | | | | | 95.0 |
| Tallow diquaternary amine | | 55.3 | | | | | | | |
| Organic solvent | | | | | | | | | |
| Heavy aromatic naphtha | | | 14.6 | | | | | | |
| Ethylene glycol monobutyl ether | | | | 17.0 | 16.5 | | | | |
| 2-butoxyethanol | | 10.0 | | | | | | | |
| Base | | | | | | | | | |
| Caustic soda | | | | 3.0 | | | | | |
| Acid | | | | | | | | | |
| Hydrochloric acid | | 7.2 | | | | | | | |
| Deionized water | | | | | | | | | 2.1 |

Alternatively, the composition can comprise from about 5 to about 25 wt. % of the iron chelant and from about 55 to about 90 wt. % of the emulsifier based on the total weight of the composition. As another alternative, the composition can comprise from about 10 to about 20 wt. % of the iron chelant and from about 60 to about 90 wt. % of the emulsifier based on the total weight of the composition.

The composition can further comprise from about 0.1 to about 10 wt. %, from about 0.1 to about 5 wt. %, or from about 0.2 to about 1 wt. % of the base or the acid based on the total weight of the composition.

Another aspect of the invention is directed to an asphalt emulsion composition for surfacing pavement. The asphalt emulsion composition can comprise the composition for preparing the asphalt emulsion as described above, and an asphalt.

The asphalt can be any bitumen product derived from crude oil, especially those ordinarily used in paving roads.

The asphalt can comprise straight asphalt, semi-blown asphalt, blown asphalt, polymer-modified asphalt, cutback asphalt, petroleum-based asphalt, tar, coal tar, bitumen, or a combination thereof.

The asphalt emulsion composition can comprise from about 0.1 to about 10 wt. % of the composition for preparing the asphalt emulsion, from about 1 to about 75 wt. % of the asphalt, and from about 20 to about 80 wt. % water, based on the total weight of the asphalt emulsion composition.

Alternatively, the asphalt emulsion composition can comprise from about 0.1 to about 5 wt. % of the composition for preparing the asphalt emulsion, from about 40 to about 70 wt. % of the asphalt, and from about 20 to about 70 wt. % water, based on the total weight of the asphalt emulsion composition. Alternatively, the asphalt emulsion composition can comprise from about 0.1 to about 2 wt. % of the composition for preparing the asphalt emulsion, from about 50 to about 65 wt. % of the asphalt, and from about 30 to about 50 wt. % water, based on the total weight of the asphalt emulsion composition.

More water may be needed to maintain flowability of the asphalt emulsion composition depending upon the climate temperature at the time of application. The water amount should be below that at which the asphalt emulsion will separate from the aggregate to avoid flotation of fines and asphalt to the surface and longer setting time.

Other additives commonly used in the paving industry can be added to the asphalt emulsion composition including thickeners, pH adjusters, modifiers, and other typical asphalt and emulsion additives, such as water softeners, adhesion promoters, breaking agents such as aluminum sulfate, peptizers, polymers, among other additives well-known in the art. Softeners, include flux, re-refined engine oil bottom (REOB), anti-strip agents, warm mix additives, vacuum tower asphalt extender (VTAE), petroleum extract, or other known compounds to make a less viscous product, improve lubricity in a mixture, and/or reduce temperature requirements. Hardeners, plastomers, and elastomers, include ethylene vinyl acetate (EVA), vinyl acetate-ethylene (VAE), styrene-butadiene-styrene (SBS), styrene butadiene (SB), styrene-butadiene rubber (SBR), SBR Latex, polychloroprene, isoprene, polybutadiene, acrylic, acrylic copolymers, ground tire rubber (GTR), crumb rubber modifier (CRM), terpolymers, polyphosphoric acid (PPA), natural or synthetic waxes, GILSONITE (also known as uintaite), Trinidad Lake asphalt, and other modifiers that are well-known in the industry and commonly used for the purpose of adding elastomeric properties and strength. Emulsion additives include stabilizers, thickeners, additives known to adjust pH, water softeners, breaking agents, peptizers, and adhesion promoters. The amount of conventional asphalt additive(s) used may be any amount that is typically used for modifying asphalts for a given application and/or asphalt product. These amounts are well-known in the field. Thus, a person of skill in the art would be able to determine what conventional asphalt additive(s) and what amount(s) is/are desirable or required to meet a given application condition or contract requirement for the emulsified asphalt composition.

A mineral aggregate can be added to the asphalt emulsion composition. Preferably, the mineral aggregate is mixed into the asphalt emulsion composition on site just prior to application to a pavement.

A polymer or latex can be added to increase the durability of the pavement. Examples include a styrene-butadiene rubber, a styrene-butadiene-styrene rubber, a chloroprene rubber, a thermoplastic resin (ethylene vinyl acetate copolymer, ethylene ethyl acrylate copolymer, and a latex (styrene-butadiene latex, a chloroprene latex, a neoprene latex).

The composition for preparing the asphalt emulsion, and asphalt emulsion composition can be prepared by conventional means well known in the paving art. For example, the asphalt emulsion composition can be prepared in a colloid mill. The components of these compositions can be mixed in any order of addition in the desired proportions in a vessel with stirring and maintained at temperatures up to about 93° C. Any solid components can be heated and liquefied prior to being charged to the vessel.

Another aspect of the invention is directed to a method of treating a surface of a pavement. The method can comprise: applying the asphalt emulsion composition as described herein to the surface of the pavement or to a layer comprising a mineral aggregate on the surface of the pavement to form a treated surface; and curing the treated surface.

Another method of treating a surface of a pavement is also provided. The method can comprise: combining the composition for preparing the asphalt emulsion as described herein, an asphalt and water to form an asphalt emulsion composition; applying the asphalt emulsion composition to the surface of the pavement or to a layer comprising a mineral aggregate on the surface of the pavement to form a treated surface; and curing the treated surface.

Yet another method of treating a surface of a pavement is also provided. The method can comprise: combining an iron chelant and an asphalt emulsion comprising asphalt, an emulsifier and water to form a surfacing composition; applying the surfacing composition to the surface of the pavement or to a layer comprising a mineral aggregate on the surface of the pavement to form a treated surface; and curing the treated surface.

These methods can further comprise mixing a mineral aggregate with the asphalt emulsion composition or surfacing composition before application.

These methods can further comprise applying a layer of mineral aggregate on the treated surface, such as before the treated surface is cured. Such an additional mineral aggregate layer can be used in chip sealing and sandwich sealing methods.

Different mineral aggregates can be used, if desired, when applying a layer of mineral aggregate on the treated surface than the mineral aggregate used in the layer comprising mineral aggregate that may be on the surface of the pavement. Likewise, mineral aggregate that may be included in the asphalt emulsion composition can be different than the mineral aggregate used as layers on the pavement surface.

The surfacing composition used in this method can comprise from about 0.1 to about 10 wt. %, from about 0.1 to about 5.0 wt. %, or from about 0.1 to about 1.0 wt. % of the iron chelant based on the total weight of the surfacing composition.

The surfacing composition used in this method can comprise from about 0.1 to about 10 wt. %, from about 0.1 to about 5.0 wt. %, or from about 0.1 to about 2.0 wt. % of the emulsifier based on the total weight of the surfacing composition.

In the methods described herein, applying the asphalt emulsion composition or applying the surfacing composition can comprise microsurfacing, chip sealing, double surface treating, triple surface treating, cape sealing, sandwich sealing, sand sealing, slurry sealing, seal coating or fog sealing.

In these methods, the asphalt emulsion composition or surfacing composition is typically applied with, or on top of a layer of mineral aggregate such as cement, slag, sand, limestone, crushed rock or stone, granite, dolomite, and gravel. Alternatively, the asphalt emulsion composition or surfacing composition can be mixed with the mineral aggregates.

Cement may be mixed with other mineral aggregates to modify the curing time of the asphalt emulsion composition or surfacing composition.

Mineral aggregates as used conventionally in the industry are suitable for the microsurfacing, chip sealing, double surface treating, triple surface treating, cape sealing, sandwich sealing, sand sealing, slurry sealing, seal coating or fog sealing methods. The Federal Highway Administration and other associations also set standards required for particular applications as is known in the art.

The mineral aggregates used in the methods described herein can be screened as desired. For example, the aggregates may range in size from anything passing through a No. 4 or No. 10 sieve, with not more than 20% passing through a No. 200 sieve, as described in ASTM C136.

The surfacing composition can comprise from about 60 to about 90 wt. % mineral aggregate, from 0 to about 2 wt. % cement, from about 1 to about 30 wt. % asphalt emulsion composition, and from about 0.1 to about 20 wt. % water, based on the total weight of the surfacing composition. Alternatively, the surfacing composition can comprise from about 70 to about 90 wt. % mineral aggregate, from 0.1 to about 1.5 wt. % cement, from about 5 to about 25 wt. % asphalt emulsion composition, and from about 1 to about 15 wt. % water, based on the total weight of the surfacing composition. Alternatively, the surfacing composition can comprise from about 80 to about 90 wt. % mineral aggregate, from 0.5 to about 1.2 wt. % cement, from about 10 to about 15 wt. % asphalt emulsion composition, and from about 2 to about 10 wt. % water, based on the total weight of the surfacing composition.

Yet another aspect of the invention is directed to a treated pavement. The treated pavement can comprise a pavement and a surface layer on an exposed surface of the pavement, the surface layer containing an iron chelant, an emulsifier, and an asphalt. The treated pavement can be prepared by any of the methods as described herein. Any of the iron chelants, emulsifiers, and asphalts as described herein can be used in preparing the treated pavement.

The treated pavement can further comprise a layer of mineral aggregate on the exposed surface of the pavement, such that the surface layer is applied on the layer of mineral aggregate.

The treated pavement can include a layer of mineral aggregate on at least a portion of the surface layer.

The surface layer of the treated pavement can further include a mineral aggregate. The treated pavement is made by curing the asphalt emulsion composition or curing composition such that water and volatile solvents are released and the asphalt hardens.

The treated pavement can comprise from about 0.01 to about 1.0 wt. %, from about 0.01 to about 0.5 wt. %, or from about 0.01 to about 0.1 wt. % of the iron chelant based on the total weight of the surface layer.

The treated pavement can comprise from about 0.01 to about 1.0 wt. %, from about 0.01 to about 0.5 wt. %, or from about 0.01 to about 0.25 wt. % of the emulsifier based on the total weight of the surface layer.

The pavement of the methods and treated pavement as described herein can comprise a primed granular base, an asphalt pavement, or a Portland cement pavement.

The pavement can be a road, a highway, a driveway, a parking lot, a runway, or any other paved surface.

Definitions

The term "alkyl," as used herein, unless otherwise specified, refers to a linear or branched hydrocarbon group, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined herein.

The term "alkenyl," as used herein, unless otherwise specified, refers to a straight or branched hydrocarbon group, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined herein.

The term "alkoxy," as used herein, refers to an alkyl group, as defined herein, appended to the parent molecular moiety through an oxygen atom.

The term "aryl," as used herein, means monocyclic, bicyclic, or tricyclic aromatic groups such as phenyl, naphthyl, tetrahydronaphthyl, indanyl and the like; optionally substituted by one or more suitable substituents, preferably 1 to 5 suitable substituents, as defined herein.

The term "cycloalkyl," as used herein, refers to a mono, bicyclic or tricyclic carbocyclic group (e.g., cyclopropyl, cyclobutyl, cyclopentyl, cyclohexyl, cycloheptyl, cyclooctyl, cyclononyl, cyclopentenyl, cyclohexenyl, bicyclo[2.2.1] heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined herein.

As used herein, the term "derivative" refers to any salt or ester of the compound or the compound having one or more suitable substituents.

The term "-ene" as used as a suffix as part of another group denotes a bivalent group in which a hydrogen atom is removed from each of two terminal carbons of the group. For example, alkylene denotes a bivalent alkyl group such as methylene (—$CH_2$—) or ethylene (—$CH_2CH_2$—). For clarity, addition of the -ene suffix is not intended to alter the definition of the principal word other than denoting a bivalent group. Thus, continuing the example above, alkylene denotes an optionally substituted linear saturated bivalent hydrocarbon group.

The term "halo" or "halogen," as used herein, refers to a fluoro, chloro, bromo or iodo group.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle" or "heterocycyl," as used herein, refers to a monocyclic, bicyclic, or tricyclic group containing 1 to 4 heteroatoms selected from N, O, $S(O)_n$, $P(O)_m$, $PR_z$, NH or $NR_z$, wherein $R_z$ is a suitable substituent, n is 0 or 2, and m is 0 or 1. Heterocyclic groups optionally contain 1, 2 or 3 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "suitable substituent" or "substituted" as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, heterocyclic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

Having described the invention in detail, it will be apparent that modifications and variations are possible without departing from the scope of the invention defined in the appended claims.

EXAMPLES

The following non-limiting examples are provided to further illustrate the present invention.

Example 1

As an initial experiment, it was determined whether iron chelants as described herein could remove free iron (III) from solution by chelation, which could then be filtered out of solution.

TD3A-83 (32% active; from Ecolab) in water and 2-butoxyethanol was used as the iron chelant in this experiment, and is referred to as Iron Chelant A.

A sample of iron (III) chloride dissolved in water was prepared as a standard. An analytical balance was used to weigh 0.519 g of $FeCl_3$ and diluted to a total weight of 242.009 g using deionized water. This stock standard was then used to make 4 solutions of approximately 20 ppm $Fe^{3+}$. A small amount of Iron Chelant A was then added to 3 of these solutions, leaving the 4th as a control. The exact weights used are shown below in Table 2.

TABLE 2

| Sample | FeCl3 Standard (g) | Solution A (g) | Iron Chelant A (% in Solution A) | Final Sample weight (g) | Fe in Solution (ppm) | Iron Chelant A in Solution (%) |
|---|---|---|---|---|---|---|
| 1 | 0.258 | 0 | 0.00 | 10.535 | 18.1 | 0 |
| 2 | 0.279 | 0.056 | 10.24 | 9.978 | 20.6 | 0.06 |
| 3 | 0.296 | 0.414 | 2.25 | 10.002 | 21.9 | 0.09 |
| 4 | 0.25 | 0.018 | 100.0 | 12.897 | 14.3 | 0.14 |

These samples were then analyzed using CHEMetrics' Iron Vacuvials® Kit, Model #K-6013 (available from CHEMetrics, Inc. of Midland, Va.) and a Hach DR 2500 spectrophotometer. The samples were filtered using a syringe and syringe filter of 0.45 μm pore size. The vials that were under vacuum were inserted into the prepared solutions and the tip was broken off, allowing a specific amount of solution to be drawn into the vial. The vials contained 1,10-phenanthroline to form an orange colored complex in direct proportion to the soluble iron concentration. The absorbance was then measured using a wavelength of 420 nm and the iron concentrations were then calculated.

A duplicate run of the same procedure was performed to verify that the data was consistent. The weights used on the second set of samples are shown below in Table 3. To make the iron standard, 0.247 g of $FeCl_3$ were dissolved into a total of 116.049 g of water.

TABLE 3

| Sample | FeCl3 Standard (g) | Diluted Iron Chelant A added (g) | Diluted Iron Chelant A % | Final weight (g) | Fe in solution (ppm) | Iron Chelant A in solution (%) |
| --- | --- | --- | --- | --- | --- | --- |
| 1 | 1.381 | 0 | 0.00 | 50.865 | 19.9 | 0 |
| 2 | 1.378 | 0.249 | 8.80 | 49.976 | 20.2 | 0.04 |
| 3 | 1.362 | 0.5 | 8.80 | 49.973 | 20.0 | 0.09 |
| 4 | 1.367 | 0.788 | 8.80 | 50.647 | 19.8 | 0.14 |

The measured absorbances were calculated based on the formula provided by CHEMetrics for the Iron Vacu-vials® Kit shown below:

$$ppm = 27.0(abs) - 0.1$$

The values recorded for the four prepared samples of Table 1 are shown in Table 4. The values recorded for the second data set are shown below in Table 5.

TABLE 4

| Sample | Iron Chelant A in solution (%) | Measured Absorbance (Abs) | Final Fe (ppm) | Initial Fe (ppm) | % Fe Removed |
| --- | --- | --- | --- | --- | --- |
| 1 | 0.00 | 0.663 | 17.8 | 18.1 | 1.6 |
| 2 | 0.06 | 0.619 | 16.6 | 20.6 | 19.5 |
| 3 | 0.09 | 0.262 | 7.0 | 21.9 | 68.1 |
| 4 | 0.14 | 0.018 | 0.4 | 14.3 | 97.3 |

TABLE 5

| Sample | Iron Chelant A in solution (%) | Measured Absorbance (Abs) | Final Fe (ppm) | Initial Fe (ppm) | % Fe Removed |
| --- | --- | --- | --- | --- | --- |
| 1 | 0.00 | 0.698 | 18.7 | 19.9 | 5.8 |
| 2 | 0.04 | 0.498 | 13.3 | 20.2 | 34.0 |
| 3 | 0.09 | 0.366 | 9.8 | 20.0 | 51.0 |
| 4 | 0.14 | 0.135 | 3.5 | 19.8 | 82.1 |

The results show a direct correlation between the amount of Iron Chelant A added and the amount of iron that is chelated and filtered from solution.

Example 2

An experiment was designed to determine whether iron chelants as described herein were effective in removing free iron from an asphalt slurry system by chelation, and whether removal of iron would reduce discoloration of paved asphalt that is observed with iron-containing aggregates.

Four emulsions were made using a tall oil fatty acid and soybean fatty acid polyalkyleneamine condensate as the emulsifier. One emulsion contained no additives and served as a control, while the other three contained a known amount of three different chelating agents—catechol, 4-tert butyl-catechol, and the Iron Chelant A of Example 1. Table 6 below shows the percentages of emulsifier, iron chelant, and solvent used to create the four emulsions.

TABLE 6

| Emulsion Sample | Emulsifier (%) | Catechol (%) | 4-tert-Butyl-catechol (%) | Iron Chelant A (%) | Glycol Ether (%) |
| --- | --- | --- | --- | --- | --- |
| 1 | 100 | 0 | 0 | 0 | 0 |
| 2 | 65.1 | 17.9 | 0 | 0 | 17.0 |
| 3 | 65.8 | 0 | 17.7 | 0 | 16.5 |
| 4 | 90.0 | 0 | 0 | 10.0 | 0 |

These emulsions were then used to create samples made to represent the formulations used in asphalt applications. Slurry seal applications contain asphalt emulsion, mineral aggregate, cement, and water. For this testing, an additional component of 10.0% iron (III) chloride, representing roughly 3.4% iron in the system, was added to help facilitate the discoloration of the asphalt samples.

To create the asphalt samples, mineral aggregate, iron (III) chloride and cement were weighed and mixed together dry. The water was then added and the material was stirred by hand. The asphalt emulsion was then added and mixed well, followed by the material being poured into a ring mold. These asphalt samples were placed in a 60° C. oven over night. The four asphalt samples were prepared as shown in Table 7:

TABLE 7

| | Asphalt Sample 1 | | | | Asphalt Sample 2 | | |
| --- | --- | --- | --- | --- | --- | --- | --- |
| Component | Theoretical (g) | Actual (g) | % of Aggregate | Component | Theoretical (g) | Actual (g) | % of Aggregate |
| Mineral Aggregate | | 85.11 | | Mineral Aggregate | | 85.17 | |
| Cement | 0.85 | 0.85 | 1 | Cement | 0.85 | 0.85 | 1 |
| FeCl3 | 8.56 | 8.54 | 10 | FeCl3 | 8.52 | 8.54 | 10 |
| Water | 4.28 | 4.28 | 5 | Water | 4.26 | 4.25 | 5 |
| Emulsion Sample 1 | 12.83 | 12.87 | 12 | Emulsion Sample 2 | 12.78 | 12.84 | 12 |

TABLE 7-continued

| | Asphalt Sample 3 | | | | Asphalt Sample 4 | | |
|---|---|---|---|---|---|---|---|
| Component | Theoretical (g) | Actual (g) | % of Aggregate | Component | Theoretical (g) | Actual (g) | % of Aggregate |
| Mineral Aggregate | | 85.30 | | Mineral Aggregate | | 85.18 | |
| Cement | 0.85 | 0.96 | 1 | Cement | 0.85 | 0.84 | 1 |
| FeCl$_3$ | 8.53 | 8.51 | 10 | FeCl$_3$ | 8.52 | 8.68 | 10 |
| Water | 4.26 | 4.37 | 5 | Water | 4.26 | 4.35 | 5 |
| Emulsion Sample 1 | 12.79 | 12.84 | 12 | Emulsion Sample 2 | 12.78 | 12.78 | 12 |

Figure 1:
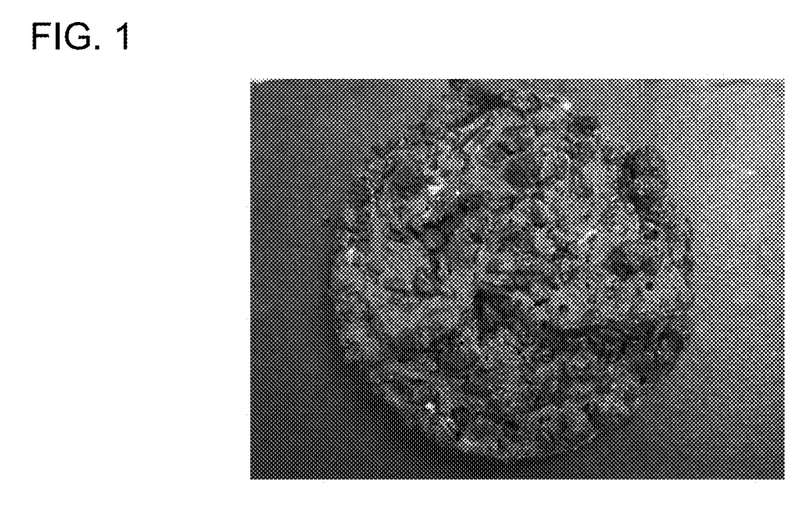
FIGS. 1-3 are photographs of asphalt compositions including iron which exhibit discoloration.
Figure 2:
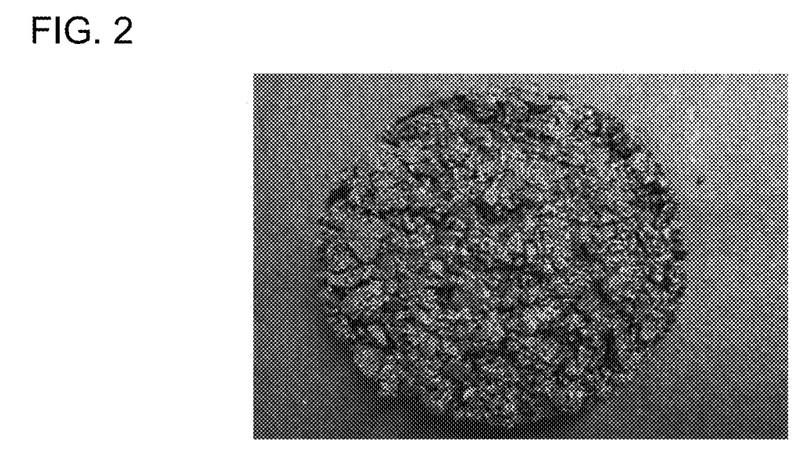
Figure 3:
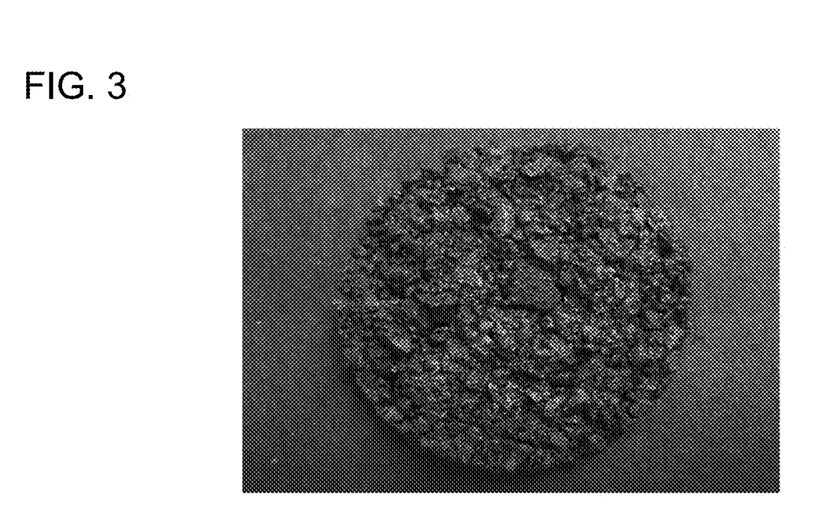
Figure 4:
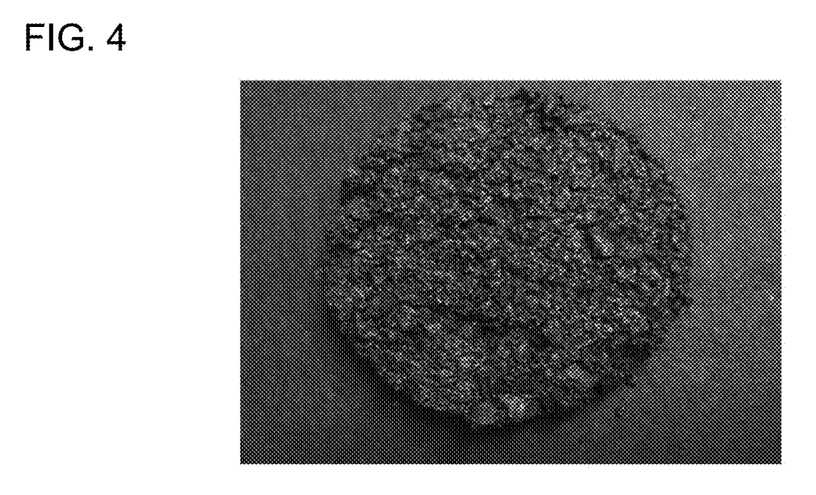
FIG. 4 is a photograph of an asphalt composition of the invention which does not exhibit discoloration.

The control Asphalt Sample 1 that was made using the emulsifier and no iron chelant (Emulsion Sample 1 of Table 6) had discoloration similar to the pavement discoloration witnessed in prior commercial slurry sealing treatments. The Asphalt Samples 2-4 made using emulsifiers that contained an additional iron chelant (Emulsion Samples 2-4 of Table 6) did not have any discoloration on the surface. FIGS. 1-4 display the color differences in the samples created.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A composition for preparing an asphalt emulsion, comprising an emulsifier and an iron chelant, wherein the iron chelant comprises:
a carboxylic acid derivative of an alkylamine having the formula:

wherein:
$R_1$, $R_2$, $R_4$, $R_5$, and $R_6$ are each individually hydrogen, $C_6$-$C_{30}$ alkyl, or —$R_7$COOH;
$R_3$ and $R_7$ are each individually alkylene;
n is 0; and
at least one of $R_1$, $R_2$, $R_4$, and $R_5$ is $C_6$-$C_{30}$ alkyl, and at least one of $R_1$, $R_2$, $R_4$, and $R_5$ is —$R_7$COOH.

2. The composition of claim 1, wherein the iron chelant further comprises catechol; or alkyl catechol.

3. The composition of claim 1, wherein:
$R_1$ is $C_8$-$C_{22}$ alkyl; $R_2$, $R_4$, and $R_5$ are each individually hydrogen or —$R_7$COOH; $R_3$ and $R_7$ are each individually $C_1$-$C_6$ alkylene; n is 0; and at least one of $R_2$, $R_4$, and $R_5$ is —$R_7$COOH.

4. The composition of claim 3, wherein $R_1$ is tallow, $R_3$ is propylene, and $R_7$ is methylene.

5. The composition of claim 1, wherein the emulsifier comprises a tallow amine, a tallow diamine, a diquaternary amine, a tallow tetramine, a tallow diquaternary amine, oleic acid, a tall oil, a tall oil resin, a tall oil imidazoline, a tall oil fatty acid, a soybean fatty acid, a tall oil fatty acid and soybean fatty acid polyalkyleneamine condensate, a lignosulphonate, a lignin, a lignin amine, an imidazoline, an amidoamine, an amidopolyamine, a triglyceride, an ethoxylate, an alkoxylate, a carboxylate, a polycarboxylate, a sulfonate, a fatty amine, a fatty acid, a rosin acid, alkylphenol alkoxylate, or combination thereof.

6. The composition of claim 1, further comprising an organic solvent, water, a base, an acid, or a combination thereof.

7. The composition of claim 6, wherein the organic solvent comprises methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

8. The composition of claim 6, wherein:
the base comprises sodium hydroxide, magnesium hydroxide, potassium hydroxide, calcium hydroxide, ammonium hydroxide, sodium carbonate, sodium bicarbonate, or a combination thereof; or
the acid comprises an inorganic acid or an organic acid.

9. The composition of claim 6, comprising:
from about 5 to about 30 wt. % of the iron chelant and about 40 to about 95 wt. % of the emulsifier based on the total weight of the composition; or
from about 5 to about 25 wt. % of the iron chelant and from about 55 to about 90 wt. % of the emulsifier based on the total weight of the composition; or
from about 10 to about 20 wt. % of the iron chelant and from about 60 to about 90 wt. % of the emulsifier based on the total weight of the composition.

10. The composition of claim 9, further comprising:
from about 0.1 to about 10 wt. %, from about 0.1 to about 5 wt. %, or from about 0.2 to about 1 wt. % of the base or the acid based on the total weight of the composition; or
from about 0.1 to about 25 wt. %, from about 5 to about 20 wt. %, or from about 10 to about 20 wt. % of the organic solvent based on the total weight of the composition; or from about 0.1 to about 10 wt. %, from about 0.1 to about 6 wt. %, or from about 0.1 to about 4 wt. % water based on the total weight of the composition.

11. The composition of claim 1, wherein the emulsifier comprises a tallow diquaternary amine, a tall oil imidazoline, a tall oil fatty acid and soybean fatty acid polyalkyleneamine condensate, or combination thereof.

12. The composition of claim 1, wherein one, two or three of $R_1$, $R_2$, $R_4$, and $R_5$ is —$R_7$COOH; each $R_3$ is individually $C_2$-$C_4$ alkylene; each $R_7$ is individually $C_1$-$C_4$ alkylene; and n is 0.

13. A composition for preparing an asphalt emulsion, comprising an emulsifier and an iron chelant, wherein the iron chelant comprises a carboxylic acid derivative of an alkylamine having the formula:

wherein:
$R_1$, $R_2$, $R_4$, $R_5$, and $R_6$ are each individually hydrogen, $C_6$-$C_{30}$ alkyl, or —$R_7$COOH;
$R_3$ and $R_7$ are each individually alkylene;
n is 1, or 2; and
at least one of $R_1$, $R_2$, $R_4$, $R_5$, and $R_6$ is $C_6$-$C_{30}$ alkyl, and at least two of $R_1$, $R_2$, $R_4$, $R_5$, and $R_6$ is —$R_7$COOH.

14. The composition of claim 13, wherein two or three of $R_1$, $R_2$, $R_4$, $R_5$, and $R_6$ is —$R_7$COOH; each $R_3$ is individually $C_2$-$C_4$ alkylene; each $R_7$ is individually $C_1$-$C_6$ alkylene; and n is 1.

15. The composition of claim 13, wherein $R_1$ is $C_8$-$C_{22}$ alkyl; $R_2$, $R_4$, $R_5$, and $R_6$ are each individually hydrogen or —$R_7$COOH; $R_3$ and $R_7$ are each individually $C_1$-$C_6$ alkylene; n is 1 or 2; and at least two of $R_2$, $R_4$, $R_5$, and $R_6$ is —$R_7$COOH.

16. The composition of claim 15, wherein $R_1$ is tallow, $R_3$ is propylene, and $R_7$ is methylene.

17. The composition of claim 13, wherein the emulsifier comprises a tallow amine, a tallow diamine, a diquaternary amine, a tallow tetramine, a tallow diquaternary amine, oleic acid, a tall oil, a tall oil resin, a tall oil imidazoline, a tall oil fatty acid, a soybean fatty acid, a tall oil fatty acid and soybean fatty acid polyalkyleneamine condensate, a lignosulphonate, a lignin, a lignin amine, an imidazoline, an amidoamine, an amidopolyamine, a triglyceride, an ethoxylate, an alkoxylate, a carboxylate, a polycarboxylate, a sulfonate, a fatty amine, a fatty acid, a rosin acid, alkylphenol alkoxylate, or a derivative or combination thereof.

18. The composition of claim 13, further comprising an organic solvent, water, a base, an acid, or a combination thereof.

19. The composition of claim 18, wherein the organic solvent comprises methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

20. The composition of claim 18, wherein:
the base comprises sodium hydroxide, magnesium hydroxide, potassium hydroxide, calcium hydroxide, ammonium hydroxide, sodium carbonate, sodium bicarbonate, or a combination thereof; or
the acid comprises an inorganic acid or an organic acid.

21. The composition of claim 18, comprising:
from about 5 to about 30 wt. % of the iron chelant and about 40 to about 95 wt. % of the emulsifier based on the total weight of the composition; or
from about 5 to about 25 wt. % of the iron chelant and from about 55 to about 90 wt. % of the emulsifier based on the total weight of the composition; or
from about 10 to about 20 wt. % of the iron chelant and from about 60 to about 90 wt. % of the emulsifier based on the total weight of the composition.

22. The composition of claim 21, further comprising:
from about 0.1 to about 10 wt. %, from about 0.1 to about 5 wt. %, or from about 0.2 to about 1 wt. % of the base or the acid based on the total weight of the composition; or
from about 0.1 to about 25 wt. %, from about 5 to about 20 wt. %, or from about 10 to about 20 wt. % of the organic solvent based on the total weight of the composition; or
from about 0.1 to about 10 wt. %, from about 0.1 to about 6 wt. %, or from about 0.1 to about 4 wt. % water based on the total weight of the composition.

23. An asphalt emulsion composition for surfacing pavement comprising the composition for preparing the asphalt emulsion of claim 1, and an asphalt.

24. The asphalt emulsion composition of claim 23, wherein:
the asphalt comprises straight asphalt, semi-blown asphalt, blown asphalt, polymer-modified asphalt, cutback asphalt, petroleum-based asphalt, tar, coal tar, bitumen, or a combination thereof; or
the asphalt emulsion composition comprises:
from about 0.1 to about 10 wt. % of the composition for preparing the asphalt emulsion, from about 1 to about 75 wt. % of the asphalt, and from about 20 to about 80 wt. % water, based on the total weight of the asphalt emulsion composition; or
from about 0.1 to about 5 wt. % of the composition for preparing the asphalt emulsion, from about 40 to about 70 wt. % of the asphalt, and from about 20 to about 70 wt. % water, based on the total weight of the asphalt emulsion composition; or
from about 0.1 to about 2 wt. % of the composition for preparing the asphalt emulsion, from about 50 to about 65 wt. % of the asphalt, and from about 30 to about 50 wt. % water, based on the total weight of the asphalt emulsion composition.

25. A method of treating a surface of a pavement comprising:
applying the asphalt emulsion composition of claim 23 to the surface of the pavement or to a layer comprising a mineral aggregate on the surface of the pavement to form a treated surface; and
curing the treated surface.

26. A method of treating a surface of a pavement comprising:
combining the composition for preparing the asphalt emulsion of claim 1, an asphalt and water to form an asphalt emulsion composition;

applying the asphalt emulsion composition to the surface of the pavement or to a layer comprising a mineral aggregate on the surface of the pavement to form a treated surface; and
curing the treated surface.

27. The method of claim 25, further comprising:
mixing the mineral aggregate with the asphalt emulsion composition or surfacing composition before application; or
applying a layer of mineral aggregate on the treated surface before it is cured.

\* \* \* \* \*

UNITED STATES PATENT AND TRADEMARK OFFICE
CERTIFICATE OF CORRECTION

| | |
|---|---|
| PATENT NO. | : 11,447,637 B2 |
| APPLICATION NO. | : 16/806416 |
| DATED | : September 20, 2022 |
| INVENTOR(S) | : Robert Gabel et al. |

It is certified that error appears in the above-identified patent and that said Letters Patent is hereby corrected as shown below:

On the Title Page

Column 2, item (56) under OTHER PUBLICATIONS section, Line 1: "Machinne"
Should read -- Machine --

Signed and Sealed this
Twenty-fifth Day of April, 2023

Katherine Kelly Vidal
*Director of the United States Patent and Trademark Office*